United States Patent
Chou et al.

(10) Patent No.: US 7,754,101 B2
(45) Date of Patent: Jul. 13, 2010

(54) SUBSTITUTED ALKYLMETAL COMPOSITIONS AND METHODS OF PREPARING THE SAME

(75) Inventors: Chun-Tzer Chou, Charlotte, NC (US); Christopher Jay Woltermann, Gastonia, NC (US)

(73) Assignee: FMC Corporation, Philadelphia, PA (US)

( * ) Notice: Subject to any disclaimer, the term of this patent is extended or adjusted under 35 U.S.C. 154(b) by 1 day.

(21) Appl. No.: 12/274,422

(22) Filed: Nov. 20, 2008

(65) Prior Publication Data

US 2009/0140200 A1    Jun. 4, 2009

Related U.S. Application Data

(60) Provisional application No. 60/991,876, filed on Dec. 3, 2007.

(51) Int. Cl.
| | |
|---|---|
| C09K 3/00 | (2006.01) |
| C07F 7/08 | (2006.01) |
| C07F 7/02 | (2006.01) |
| C07F 7/04 | (2006.01) |
| C07F 7/00 | (2006.01) |
| B01J 31/00 | (2006.01) |

(52) U.S. Cl. ............... 252/182.33; 252/182.3; 556/12; 556/400; 556/427; 556/465; 556/466; 502/102

(58) Field of Classification Search ............ 252/182.3, 252/182.33; 546/298; 556/446, 427, 12, 556/400, 465; 502/102
See application file for complete search history.

(56) References Cited

U.S. PATENT DOCUMENTS

2007/0249838 A1* 10/2007 Woltermann et al. ........ 546/298

OTHER PUBLICATIONS

Doudouh et al. "TMSCH$_2$Li-LiDMAE: a new nonnucleophilic reagent for C-2 lithiation of halopyridines", *Tetrahedron* 62(26):6166-6171 (2006).

Harada et al. "Generation of 1-(Trimethylsilylmethyl)-1,2-alkadienylzines and Their Use in Preparation of Functionalized Propargylsilanes", *Tetrahedron Letters* 36(5):723-724 (1995).

Notification of Transmittal of the International Search Report and the Written Opinion of the International Searching Authority, or the Declaration, corresponding to International Application No. PCT/US2008/013275 mailed Mar. 17, 2009.

* cited by examiner

*Primary Examiner*—Ling-Siu Choi
*Assistant Examiner*—Monique Peets
(74) *Attorney, Agent, or Firm*—Myers Bigel Sibley & Sajovec, PA

(57) ABSTRACT

Substituted alkylmetal solutions and a method for making the same wherein the solutions include (a) a substituted alkylmetal compound of the formula of $M\text{-}CH_2\text{—}W(R_a)(R_b)(R_c)$ at a concentration of greater than 1.0M; (b) a hydrocarbon solvent; and (c) an amine cosolvent.

8 Claims, No Drawings

SUBSTITUTED ALKYLMETAL COMPOSITIONS AND METHODS OF PREPARING THE SAME

CROSS-REFERENCE TO RELATED APPLICATIONS

This application claims the benefit of, and incorporates herein by reference in its entirety, the following U.S. Provisional Application: U.S. Provisional Application No. 60/991,876, filed Dec. 3, 2007.

FIELD OF THE INVENTION

The present invention relates to compositions and methods that include alkylmetal reagents.

BACKGROUND OF THE INVENTION (Trimethylsilylmethyl)lithium ($TMSCH_2Li$) and other substituted alkylmetal reagents may be useful in a number of organic transformations, including, e.g., polymer initiation reactions, the Peterson Olefination reaction and deprotonation and/or halogen-metal exchange reactions involving pyridines.

However, one drawback with using substituted alkylmetal reagents, and particularly reagents such as $TMSCH_2Li$ is that they may have modest solubility in hydrocarbon solvents. For example, one molar solutions of $TMSCH_2Li$ in hexanes or pentane may be available, but even at this low concentration, the $TMSCH_2Li$ may readily crystallize out of solution if stored below room temperature. The resulting $TMSCH_2Li$ crystals may be relatively large, and so may clog dispensing apparatuses. Such crystals may also be relatively slow to redissolve in hydrocarbon solvents.

It is known that the solubility of substituted alkylmetal reagents may be improved by adding ether co-solvents. However, the stability of the alkylmetal reagents with ether co-solvents is not suitable for storage over extended periods of time.

As such, it would be desirable to be able to increase the concentration of substituted methylmetal reagents in hydrocarbon solutions. It would also be desirable for such solutions to remain stable for relatively long periods of time.

SUMMARY OF THE INVENTION

Provided according to some embodiments of the invention are solutions that include a compound having the formula of $M-CH_2-W(R_a)(R_b)(R_c)$, wherein $R_a$, $R_b$ and $R_c$ are independently alkyl or aryl, W is silicon or tin, and M is selected from the group consisting of lithium, sodium, potassium, cesium, manganese, zinc and magnesium. The solution also may include a hydrocarbon solvent and an amine cosolvent. In some embodiments, the compound includes a silylalkyllithium. In particular embodiments, the substituted alkylmetal may include (trimethylsilylmethyl)lithium ($TMSCH_2Li$). The compound may be at a concentration of greater than 1.0M. According to some embodiments of the invention, the amine cosolvent has the formula of $N(R_1)(R_2)(R_3)$, wherein $R_1$, $R_2$ and $R_3$ are each independently a hydrogen, alkyl including 1 to 20 carbon atoms or aryl, and wherein, optionally, $R_1$, $R_2$ and/or $R_3$ together form a cyclic hydrocarbon ring.

Also provided according to some embodiments of the invention are methods of increasing the concentration and lowering the crystallization temperature of a substituted alkylmetal solution. Such methods may include adding an amine cosolvent to a compound of the formula Of $M-CH_2-W(R_a)(R_b)(R_c)$ in a hydrocarbon solvent; and forming a substituted alkylmetal-amine adduct. In some embodiments, the substituted alkylmetal-amine adduct is present at a concentration of greater than 1.0M.

DETAILED DESCRIPTION OF EMBODIMENTS OF THE INVENTION

The invention is described more fully hereinafter. This invention may, however, be embodied in many different forms and should not be construed as limited to the embodiments set forth herein. Rather, these embodiments are provided so that this disclosure will be thorough and complete, and will fully convey the scope of the invention to those skilled in the art.

The terminology used herein is for the purpose of describing particular embodiments only and is not intended to be limiting of the invention. As used herein, the singular forms "a", "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. Additionally, for all embodiments described inclusively, such as by using the terms "including" or "comprising," it will be understood that less inclusive embodiments, such as those using the terms "consisting" and "consisting essentially of" are also meant to be encompassed herein. Furthermore, it will be understood that as used herein, the term "and/or" includes any and all combinations of one or more of the associated listed items.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

As used herein, the term "alkyl" refers to a straight, branched or cyclic hydrocarbon containing from 1 to 20 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, and the like. "Lower alkyl" as used herein, is a subset of alkyl and refers to a hydrocarbon group containing from 1 to 4 carbon atoms. Representative examples of lower alkyl include, but are not limited to, methyl, ethyl, n-propyl, iso-propyl, n-butyl, iso-butyl, tert-butyl, and the like. The term "alkyl" is intended to include both unsubstituted alkyl and substituted alkyl, unless otherwise indicated. For example, an alkyl may be substituted with one or more heteroatoms (e.g., oxygen, sulfur and/or nitrogen).

As used herein, the term "aryl" refers to a monocyclic carbocyclic ring system or a bicyclic carbocyclic fused ring system having one or more aromatic rings. Representative examples of aryl include, azulenyl, indanyl, indenyl, naphthyl, phenyl, tetrahydronaphthyl, and the like. The term "aryl" is intended to include both substituted and unsubstituted aryl unless otherwise indicated. For example, an aryl may be substituted with one or more heteroatoms (e.g., oxygen, sulfur and/or nitrogen).

As used herein, the term "silyl" refers to a straight, branched or cyclic alkyl analog whereby at least one carbon atom in the alkyl, as defined herein, is substituted with a silicon atom.

Provided herein according to some embodiments of the invention are solutions that include (a) a substituted alkylmetal compound having the formula of M-$CH_2$—$W(R_a)(R_b)(R_c)$, wherein $R_a$, $R_b$ and $R_c$ are each independently alkyl or aryl, W is Si or Sn, and M is selected from the group consisting of lithium, sodium, potassium, cesium, manganese, zinc and magnesium and the substituted alkylmetal compound may be at a concentration of greater than 1.0M; (b) a hydrocarbon solvent; and (c) an amine cosolvent. In such solutions, the substituted alkylmetal compound may or may not form an adduct with the amine cosolvent by deprotonizing the substituted alkylmetal compound.

Thus, in some embodiments, the substituted alkylmetal compound is a silylalkyllithium. In particular embodiments, the substituted alkylmetal compound may include (trimethylsilylmethyl)lithium ($TMSCH_2Li$). Mixtures of two or more different substituted alkylmetal reagents may also be used.

Any suitable hydrocarbon solvent may be used. However, exemplary hydrocarbon solvents include pentane, hexane, heptane, and the like. The hydrocarbon may be a straight chain, branched and/or cyclic hydrocarbon, and mixtures of straight, branched and/or cyclic hydrocarbons may be used. Additionally, in some embodiments, the hydrocarbon solvent is essentially dry. Mixtures of two or more different hydrocarbon solvents may also be used.

Any suitable amine cosolvent may be used, including primary, secondary and/or tertiary amines. In some embodiments, the amine cosolvent includes an amine having the formula of $N(R_1)(R_2)(R_3)$, wherein $R_1$, $R_2$ and $R_3$ are each independently hydrogen, alkyl or aryl. In particular embodiments, the amine cosolvent includes an amine having the formula of $N(R_1)(R_2)(R_3)$, wherein $R_1$, $R_2$ and $R_3$ are each independently an alkyl that includes 1 to 20 carbons. In specific embodiments thereof, $R_1$, $R_2$ and/or $R_3$ together may form a cyclic hydrocarbon ring. As such, exemplary amines include but not limited to trimethylamine, triethylamine, tripropylamine, diethylmethylamine, diethylpropylamine, N-methylpiperidine, N-methylpyrrolidine, and the like. In some embodiments, the amine cosolvent includes an amine that includes aromatic groups and/or heteroaromatic groups. Exemplary aromatic tertiary amines include but not limited to triphenylamine, diethylphenylamine, dimethylphenylamine, ethyldiphenylamine, methyldiphenylamine, and the like. Furthermore, in some embodiments, the amine cosolvent may be a polyamine, such as a diamine. Mixtures of two or more different types of amine cosolvents may also be used.

Any suitable concentration of amine cosolvent may be used. However, in some embodiments, the amine cosolvent is present at a concentration in a range of about 1 weight percent to about 85 weight percent of the total weight of the solution. Furthermore, in particular embodiments, the amine cosolvent is present at a concentration in a range of about 1 to about 30 mole percent relative to the molar amount of the substituted alkylmetal compound.

The solutions according to some embodiments of the invention may include a relatively high concentration of the substituted alkylmetal compound. For example, in some embodiments, the concentration of the substituted alkylmetal compound is greater than about 1 M, in some embodiments greater than 1.5 M, in some embodiments greater than 2 M, in some embodiments greater than 2.5 M, and in some embodiments, greater than 3 M.

The solutions provided according to some embodiments of the invention may be relatively stable and so may be advantageously utilized when the solutions need to be stored for a relatively long period of time. For example, in some embodiments of the invention, the concentration of the substituted alkylmetal compound (e.g., $TMSCH_2Li$) in solution decreases by less than about 2% in 24 days when the solution is held at a temperature in a range of about 0° C. and about 40° C. Furthermore, in some embodiments, the concentration of the substituted alkylmetal compound in the solution is essentially constant for 24 days when the solution is held at a temperature in a range of about 0° C. and about 5° C.

Also provided herein are methods of increasing the concentration and lowering the crystallization temperature of a solution comprising a substituted alkylmetal compound by forming a solution according to embodiments of the invention. In some embodiments of the invention, such methods include adding an amine cosolvent to a substituted alkylmetal compound in a hydrocarbon solvent. One skilled in the art will recognize that when the substituted alkylmetal compound is added to the amine co-solvent that a proton will be removed from the alkylmetal compound and an alkylmetal amide is formed. In some embodiments, the substituted alkylmetal compound and the amine cosolvent form a substituted alkylmetal-amine adduct, and in particular embodiments, the substituted alkylmetal-amine adduct is present at a concentration of greater than 1.0M. In some embodiments, only a portion of the substituted alkylmetal compound forms an adduct with the amine cosolvent.

The substituted alkylmetal compound is typically dissolved in the hydrocarbon solvent. However, in some embodiments, the substituted alkylmetal compound may not be completely dissolved in the hydrocarbon solvent until suitable interaction with the amine cosolvent. The resulting alkylmetal solutions are homogenous or essentially homogeneous.

Substituted alkylmetal compounds, hydrocarbon solvents and amine adducts that may be used in methods according to embodiments of the invention are described elsewhere herein.

Any suitable amount of amine cosolvent may be added in methods according to embodiments of the invention. However, in some embodiments, the amine cosolvent is added such that the concentration of the amine in the final substituted alkylmetal-amine solution is in a range of about 1 weight percent to about 85 weight percent. Furthermore, in particular embodiments, the amine cosolvent is added such that the concentration of the amine in the final substituted alkylmetal-amine solution is in a range of about 1 to about 30 mole percent relative to the substituted alkylmetal compound.

The substituted alkylmetal-amine solutions formed according to some embodiments of the invention may include a relatively high concentration of substituted alkylmetal compound. For example, in some embodiments, the concentration of substituted alkylmetal compound in the resulting substituted alkylmetal-amine solution is greater than about 1 M, in some embodiments greater than 1.5 M, in some embodiments greater than 2 M, in some embodiments greater than 2.5 M, and in some embodiments, greater than 3 M.

The substituted alkylmetal-amine solutions provided according to some embodiments of the invention may be relatively stable and so may be advantageously used when the substituted alkylmetal-amine solutions need to be stored for a relatively long period of time. For example, in some embodiments of the invention, the concentration of substituted alkylmetal compound in solution decreases by less than about 2% in 24 days when the solution is held at a temperature in a range of about 0° C. and about 40° C. Furthermore, in some embodiments, the concentration of the substituted alkylmetal compound in the solution is essentially constant for 24 days when the solution is held at a temperature in a range of about 0° C. and about 5° C.

The present invention will now be described in more detail with reference to the following examples. However, these examples are given for the purpose of illustration and are not to be construed as limiting the scope of the invention

EXAMPLES

Example 1

Exemplary Preparation of a TMSCH$_2$Li/amine Solution

A 3L three necked round bottom Morton flask was fitted with a mechanical stirrer, a 500 mL pressure-equalizing addition funnel, and a Claisen adapter fitted with a reflux condenser, thermocouple and an argon inlet. The apparatus was oven-dried overnight at 125° C., assembled hot and allowed to cool to room temperature under a purge of argon. Using a pressure filter, lithium metal dispersion was washed free of mineral oil with hexane (5×100 mL) and pentane (2×100 mL). The resultant lithium powder was dried with a stream of argon at a pressure of 3 psi and gentle heat. Once cool, the lithium metal (50 g, 7.2 mol, 2.4 equiv.) was transferred to the reaction flask with 700 mL of hexane. The reaction mixture was then stirred at approximately 350 RPM, heated to the reflux temperature of hexane (67-68° C.). Once at reflux, the heating mantle was removed and the chlorotrimethylsilane (379.55 g, 3.0 mol, 1.0 equiv.) was added dropwise at the feed rate that would provide enough of an exothermic reaction to sustain a steady reflux. The total feed time was 2 hours 50 minutes. This reaction was allowed to stir overnight at 120 RPM. The following day, the stirring was increased to approximately 300 RPMs. Triethylamine (45.6 g, 0.46 mol) was added dropwise over a period of 5 minutes. An exotherm of 1.5° C. was noted. This was allowed to stir for approximately one hour. The mixture was then heated gently to 30° C. This was then transferred to a pressure funnel with a medium porosity of 10-16 microns. Filtration produced a clear, very slightly colored material. The amount recovered was 798.7 g with a yield of 86%. Total base=36.3% (including triethylamine), Active=30.4%.

Example 2

Using the sample prepared in Example 1, the stability of the formulation was assessed by determining the % loss over time and by visual assessment of the solutions. The results are provided in Table 1. The % loss was determined by active base titration (Watson Eastham titration).

TABLE 1

| Temp (° C.) | Total Base | Active | % Loss | % Loss/Day | Days | Remarks |
|---|---|---|---|---|---|---|
| start | 35.5 | 27.9 | N/A | N/A | 0 | Total base includes TEA |
| 20 | 34.9 | 27.7 | 0.72 | 0.10 | 7 | Sample is clear. |
| 20 |  | 27.7 | 0.72 | 0.03 | 24 | Sample is clear with hint of yellow. |

TABLE 1-continued

| Temp (° C.) | Total Base | Active | % Loss | % Loss/Day | Days | Remarks |
|---|---|---|---|---|---|---|
| 20 |  | 27.5 | 1.43 | 0.04 | 32 | Sample is clear with hint of yellow. |
| 40 | 35.2 | 27.8 | 0.36 | 0.05 | 7 | Sample is clear. |
| 40 |  | 27.5 | 1.43 | 0.06 | 24 | Sample is slightly yellow and has a slight haze. |
| 0 | 35.6 | 27.9 | 0 | 0 | 7 | Sample is clear. |
| 0 |  | 28.0 | −0.36 | −0.01 | 24 | Sample is clear. |
| 0 |  | 27.6 | 1.08 | 0.03 | 32 | Sample is clear, but with a small crystal formation. |

Note:
An additional sample held at 0° C. developed a small crystal at 25 days.

Having thus described certain embodiments of the present invention, it is to be understood that the invention defined by the appended claims is not to be limited by particular details set forth in the above description as many apparent variations thereof are possible without departing from the spirit or scope thereof as hereinafter claimed. The following claims are provided to ensure that the present application meets all statutory requirements as a priority application in all jurisdictions and shall not be construed as setting forth the full scope of the present invention.

The invention claimed is:

1. A solution comprising
  (a) a substituted alkylmetal compound having the formula of M-CH$_2$—W(R$_a$)(R$_b$)(R$_c$), wherein R$_a$, R$_b$ and R$_c$ are each independently alkyl or aryl, W is silicon or tin, and M is selected from the group consisting of lithium, sodium, potassium, cesium, manganese, zinc and magnesium, said compound having a concentration of greater than 1.0M; and
  (b) a solvent consisting essentially of a hydrocarbon solvent and
    an amine cosolvent.

2. The solution of claim 1, wherein the substituted alkylmetal compound comprises (trimethylsilylmethyl) lithium (TMSCH$_2$Li).

3. The solution of claim 1, wherein the amine cosolvent comprises an amine having the formula of N(R$_1$)(R$_2$)(R$_3$), wherein R$_1$, R$_2$ and R$_3$ are each independently hydrogen, alkyl or aryl, and wherein, optionally, R$_1$, R$_2$ and/or R$_3$ together form a cyclic hydrocarbon ring.

4. The solution of claim 3, wherein at least one of R$_1$, R$_2$ and R$_3$ comprises at least one heteroatom selected from the group consisting of O, N and S.

5. The solution of claim 1, wherein the amine cosolvent is present at a concentration in a range of about 1 weight percent to about 85 weight percent of the total weight of the solution.

6. The solution of claim 1, wherein the amine cosolvent is present at a concentration in a range of about 1 to about 30 mole percent relative to the substituted alkylmetal compound.

7. The solution of claim 1, wherein the concentration of the substituted alkylmetal compound in the solution decreases by less than about 2% in 24 days when the solution is held at a temperature in a range of about 0° C. and about 40° C.

8. The solution of claim 1, wherein the concentration of the substituted alkylmetal compound in the solution is essentially constant for 24 days when the solution is held at a temperature in a range of about 0° C. and about 5° C.

* * * * *